United States Patent [19]

Staniforth et al.

[11] Patent Number: 5,858,412

[45] Date of Patent: Jan. 12, 1999

[54] SUSTAINED RELEASE FORMULATIONS UTILIZING PHARMACEUTICAL EXCIPIENT HAVING IMPROVED COMPRESSIBILITY WITH MODIFIED MICROCRYSTALLINE

[75] Inventors: John N. Staniforth, Bath, England; Bob E. Sherwood, Amenia; Edward A. Hunter, Glenham, both of N.Y.

[73] Assignee: Edward Mendell Co., Inc., Patterson, N.Y.

[21] Appl. No.: 982,224

[22] Filed: Dec. 17, 1997

Related U.S. Application Data

[60] Division of Ser. No. 676,654, Jul. 8, 1996, Pat. No. 5,741,524, which is a continuation-in-part of Ser. No. 486,183, Jun. 7, 1995, Pat. No. 5,725,883, which is a continuation-in-part of Ser. No. 370,576, Jan. 9, 1995, Pat. No. 5,585,115.

[51] Int. Cl.$^6$ .................................................. A61K 9/14
[52] U.S. Cl. ........................ 424/489; 424/494; 424/468; 424/480; 424/486; 424/487; 424/488
[58] Field of Search ..................... 424/489, 494, 424/480, 486, 487, 468, 490, 461

[56] References Cited

U.S. PATENT DOCUMENTS

| | | | |
|---|---|---|---|
| H1229 | 9/1993 | McGinley et al. | 426/654 |
| 3,023,104 | 2/1962 | Battista et al. | 99/1 |
| 3,067,037 | 12/1962 | Herald et al. | 99/139 |
| 3,141,875 | 7/1964 | Battista . | |
| 3,539,365 | 11/1970 | Durand et al. | 106/197 |
| 3,573,058 | 3/1971 | Tiemstra | 99/1 |
| 4,109,018 | 8/1978 | Thompson | 426/62 |
| 4,143,163 | 3/1979 | Hutchinson et al. | 426/96 |
| 4,156,021 | 5/1979 | Richardson | 426/104 |
| 4,159,345 | 6/1979 | Takeo . | |
| 4,219,580 | 8/1980 | Torres | 426/549 |
| 4,232,052 | 11/1980 | Nappen | 426/601 |
| 4,664,915 | 5/1987 | Simonian | 424/128 |
| 4,744,987 | 5/1988 | Mehra . | |
| 4,748,027 | 5/1988 | Schou et al. | 426/96 |
| 4,814,195 | 3/1989 | Yokoyama et al. | 426/633 |
| 4,911,946 | 3/1990 | Singer et al. | 426/658 |
| 4,946,685 | 8/1990 | Edgren et al. | 424/472 |
| 4,980,193 | 12/1990 | Tuason, Jr. et al. | 426/654 |
| 5,011,701 | 4/1991 | Baer et al. | 426/573 |
| 5,019,397 | 5/1991 | Wong et al. . | |
| 5,026,569 | 6/1991 | Forand | 426/549 |
| 5,030,400 | 7/1991 | Danielson et al. | 264/101 |
| 5,075,115 | 12/1991 | Brine | 424/486 |
| 5,126,145 | 6/1992 | Evenstad et al. | 424/465 |
| 5,132,128 | 7/1992 | Rockland | 426/658 |
| 5,158,798 | 10/1992 | Fung et al. | 426/602 |
| 5,192,569 | 3/1993 | McGinley et al. | 426/96 |
| 5,209,942 | 5/1993 | Bauer et al. | 426/573 |
| 5,322,698 | 6/1994 | Kovacs et al. | 424/480 |
| 5,338,562 | 8/1994 | Humphreys | 426/603 |
| 5,366,742 | 11/1994 | Tuason, Jr. et al. | 426/96 |
| 5,429,830 | 7/1995 | Janovsky et al. | 426/94 |
| 5,441,731 | 8/1995 | Jaxa-Chamiec et al. . | |
| 5,441,753 | 8/1995 | McGinley et al. | 426/96 |
| 5,447,729 | 9/1995 | Belenduik et al. . | |
| 5,462,761 | 10/1995 | McGinley et al. | 424/573 |
| 5,505,982 | 4/1996 | Krawczyk et al. | 426/660 |

FOREIGN PATENT DOCUMENTS

| | | |
|---|---|---|
| 1261261 | 9/1989 | Canada . |
| 0609976 | 8/1994 | European Pat. Off. . |
| 9014017 | 11/1990 | WIPO . |
| 9212633 | 8/1992 | WIPO . |
| 9312768 | 7/1993 | WIPO . |
| 9406309 | 3/1994 | WIPO . |
| 9520326 | 8/1995 | WIPO . |

OTHER PUBLICATIONS

Machines Collette High Shear Mixer Granulator Promotional Literature (date unknown).

*Primary Examiner*—Jose G. Dees
*Assistant Examiner*—Michael A. Williamson
*Attorney, Agent, or Firm*—Davidson, Davidson & Kappel, LLC

[57] ABSTRACT

Sustained release formulations include an augmented microcrystalline cellulose, an active agent, and a sustained release carrier and methods for making same are disclosed.

36 Claims, No Drawings

SUSTAINED RELEASE FORMULATIONS UTILIZING PHARMACEUTICAL EXCIPIENT HAVING IMPROVED COMPRESSIBILITY WITH MODIFIED MICROCRYSTALLINE

This application is a division of U.S. patent application Ser. No. 08/676,654 filed Jul. 8, 1996, now U.S. Pat. No. 5,741,524, which is a continuation-in-part of U.S. patent application Ser. No. 08/486,183 filed Jun. 7, 1995, now U.S. Pat. No. 5,725,883, which is a continuation-in-part of U.S. patent application Ser. No. 08/370,576 filed Jan. 9, 1995, now U.S. Pat. No. 5,585,115.

BACKGROUND OF THE INVENTION

The present invention relates to sustained-release solid dosage forms such as, e.g. tablets or capsules, which include one or more active ingredients and one or more novel excipients having desirable characteristics suitable for use in wet-granulation processes.

In order to prepare a compressed sustained-release solid dosage form containing one or more active ingredients (such as drugs), it is necessary that the material to be compressed into the dosage form possess certain physical characteristics which lend themselves to processing in such a manner. Among other things, the material to be compressed must be free-flowing, must be lubricated, and, importantly, must possess sufficient cohesiveness to insure that the solid dosage form remains intact after compression.

In the case of tablets, a tablet is formed by applying pressure to the material to be tableted, e.g. with a tablet press. A tablet press includes a lower punch which fits into a die from the bottom and a upper punch having a corresponding shape and dimension which enters the die cavity from the top after the tableting material fills the die cavity. A tablet is formed by filling the die with a tableting material and then applying pressure to the tableting material by the lower and upper punches. The ability of the tableting material to flow freely into the die is important in order to insure that there is a uniform filling of the die and a continuous movement of the material a dispenser, e.g. a feeder hopper. The compressed dosage form, e.g. tablets, must also be self-lubricating for ease of ejection from the punch faces.

Since most drugs do not exhibit these desirable characteristics, additives, i.e. pharmaceutical excipients, which impart the desired characteristics to the material(s) are used. Typically, the material to be compressed into a solid dosage form includes one or more excipients which impart the desired free-flowing, lubrication, and cohesive properties to the drug(s) to be formulated into a dosage form.

Commonly used lubricants for producing tablets that are readily ejected from the tableting machine include magnesium stearate and calcium stearate. Such lubricants are commonly included in the final tableted product in amounts of less than 1% by weight.

In addition to lubricants, solid dosage forms often contain diluents. Diluents are frequently added in order to increase the bulk weight of the material to be tableted in order that the tablet is a practical size for compression. This is often necessary where the dose of the drug is relatively small.

Another commonly used class of excipients in solid dosage forms are binders. Binders are agents which impart cohesive qualities to the powdered material(s). Commonly used binders include starch, and sugars such as sucrose, glucose, dextrose, and lactose.

Disintegrants are often included in order to ensure that the ultimately prepared compressed solid dosage form has an acceptable disintegration rate in an environment of use (such as the gastrointestinal tract). Typical disintegrants include starch derivatives and salts of carboxymethylcellulose.

There are three general methods of preparation of the materials to be included in the solid dosage form prior to compression: (1) dry granulation; (2) direct compression; and (3) wet granulation.

Dry granulation procedures may be utilized where one of the constituents, either the drug or the diluent, has sufficient cohesive properties to be tableted. The method includes mixing the ingredients, slugging the ingredients, dry screening, lubricating and finally compressing the ingredients.

In direct compression, the powdered material(s) to be included in the solid dosage form is compressed directly without modifying the physical nature of the material itself.

The wet granulation procedure includes mixing the powders to be incorporated into the dosage form in, e.g., a twin shell blender or double-cone blender and thereafter adding solutions of a binding agent to the mixed powders to obtain a granulation. Thereafter, the damp mass is screened, e.g., in a 6- or 8-mesh screen and then dried, e.g., via tray drying, the use of a fluid-bed dryer, spray-dryer, radio-frequency dryer, microwave, vacuum, or infra-red dryer.

The use of direct compression is limited to those situations where the drug or active ingredient has a requisite crystalline structure and physical characteristics required for formation of a pharmaceutically acceptable tablet. In particular, for solid dosage forms wherein the drug itself is to be administered in a relatively high dose (e.g., the drug itself comprises a substantial portion of the total tablet weight), it is necessary that the drug(s) itself have sufficient physical characteristics (e.g., cohesiveness) for the ingredients to be directly compressed. However, for active agents which can be mixed with excipients for tableting, it is known to include one or more excipients which make the direct compression method applicable to drugs or active ingredients which do not possess the requisite physical properties.

Typically, however, excipients are added to the formulation which impart good flow and compression characteristics to the material as a whole which is to be compressed. Such properties are typically imparted to these excipients via e.g., a pre-processing step such as wet granulation, slugging, spray drying, spheronization, or crystallization. Useful direct compression excipients include processed forms of cellulose, sugars, and dicalcium phosphate dihydrate, among others.

Microcrystalline cellulose, a processed cellulose, has been utilized extensively in the pharmaceutical industry as a direct compression vehicle for solid dosage forms. Microcrystalline cellulose is commercially available under the tradename EMCOCEL® from Edward Mendell Co., Inc. and as Avicel® from FMC Corp. Compared to other directly compressible excipients. microcrystalline cellulose is generally considered to exhibit superior compressibility and disintegration properties.

Another limitation of direct compression as a method of tablet manufacture is tablet size. If the amount of active ingredient is high, a pharmaceutical formulator may choose to wet granulate the active with other excipients to attain an acceptably sized tablet with the desired compact strength. Usually the amount of filler/binder or excipients needed in wet granulation is less than that required for direct compression since the process of wet granulation contributes to some extent toward the desired physical properties of a tablet. Thus, despite the advantages of direct compression (such as reduced processing times and costs), wet granulation is widely used in the industry in the preparation of solid dosage forms. Many of those skilled in the art prefer wet granulation as compared to direct compression because this method has a greater probability of overcoming any problems associated with the physical characteristics of the various ingredients in the formulation, thereby providing a material which has the requisite flow and cohesive characteristics necessary to obtain an acceptable solid dosage form.

The popularity of the wet granulation process as compared to the direct compression process is based on at least three advantages. First, wet granulation provides the material to be compressed with better wetting properties, particularly in the case of hydrophobic drug substances. The addition of a hydrophilic excipient makes the surface of a hydrophobic drug more hydrophilic, facilitating disintegration and dissolution. Second, the content uniformnity of the solid dosage forms is generally improved. Via the wet granulation method, all of the granules thereby obtained should contain approximately the same amount of drug. Thus, segregation of the different ingredients of the material to be compressed (due to different physical characteristics such as density) is avoided. Segregation is a potential problem with the direct compression method. Finally, the particle size and shape of the particles comprising the granulate to be compressed are optimized via the wet granulation process. This is due to the fact that when a dry solid is wet granulated, the binder "glues" particles together, so that they agglomerate in the granules which are more or less spherical.

Due to the popularity of microcrystalline cellulose as an excipient, pharmaceutical formulators have deemed it desirable to include this excipient in formulations that are wet granulated prior to tableting. Unfortunately, currently-available microcrystalline cellulose does not hold to the typical principle that the amount of filler/binder needed in wet granulation is less than that in direct compression. It is known that the exposure of the microcrystalline cellulose to moisture in the wet granulation process severely reduces the compressibility of this excipient. The loss of compressibility of microcrystalline cellulose is particularly problematic where the formulation dictates that the final product will be relatively large in the environment of use. For example, if a pharmaceutical formulator desires to prepare a solid oral dosage form of a high dose drug, and the use of the wet granulation technique is deemed necessary, the loss of compressibility of the microcrystalline cellulose dictates that a larger amount of this material may be needed to obtain an acceptably compressed final product. The additional amount of microcrystalline cellulose needed adds cost to the preparation, but more importantly adds bulk, making the product more difficult to swallow.

The loss of compressibility of microcrystalline cellulose when exposed to wet granulation has long been considered a problem in the art for which there has been no satisfactory solution.

Attempts have been made to provide an excipient having high compressibility, a small bulk (high apparent density), and good flowability, while being capable of providing satisfactory disintegration of the solid dosage form, which is applicable to wet granulation as well as to dry granulation and direct compression methods for preparation of solid dosage forms.

For example, U.S. Pat. No. 4,159,345 (Takeo, et al.) describes an excipient which consists essentially of a microcrystalline cellulose having an average degree of polymerization of 60 to 375 and obtained through acid hydrolysis or alkaline oxidative degradation of a cellulosic substance selected from linters, pulps and regenerated fibers. The microcrystalline cellulose is said to be a white cellulosic powder having an apparent specific volume of 1.6–3.1 cc/g, a repose angle of 35° to 42°, a 200-mesh sieve residue of 2 to 80% by weight and a tapping apparent specific volume of at least 1.4 cc/g.

In U.S. Pat. No. 4,744,987 (Mehra, et al.), a particulate co-processed microcrystalline cellulose and calcium carbonate composition is described wherein the respective components are present in a weight ratio of 75:25 to 35:65. The co-processed composition is said to be prepared by forming a well-dispersed aqueous slurry of microcrystalline cellulose and calcium carbonate and then drying the slurry to yield a particulate product. The combination of these two ingredients is said to provide a lower cost excipient which has tableting characteristics similar to those of microcrystalline cellulose and which would satisfy a need for an economical excipient with good performance that is desired by the vitamin market.

European Patent Application EP 0609976A1 (assigned to Asahi Kasei Kabushiki Kaisha) describes an excipient comprising white powdery microcrystalline cellulose having an average degree of polymerization of from 100 to 375, preferably from 190 to 210, and an acetic acid holding capacity of 280% or more, preferably from 290 to 370%. The excipient is said to exhibit high compactability and a high rate of disintegration and is said to be obtained by heat-treating an aqueous dispersion of purified cellulose particles, which has a solids content of 40% or less by weight, at 100° C. or more, followed by drying, or by subjecting an aqueous dispersion of purified cellulose particles having a solids content of 23% or less by weight to thin film-forming treatment and drying the resultant thin film. The excipient is said to possess a high compressibility, and a good balance of compactability and rate of disintegration.

Due to the loss of compressibility, microcrystalline cellulose has typically only been used in immediate release formulations prepared via direct compression. Although the properties of microcrystalline cellulose are well-suited for the preparation of immediate release dosage forms, due to the problems associated with use of microcrystalline cellulose in wet-granulation, it is not well-adapted for use in sustained-release dosage forms which are typically prepared by wet-granulation.

There still remains a need in the industry for sustained-release dosage forms utilizing excipients possessing excellent compressibility whether utilized in a direct compression or wet granulation procedure.

OBJECTS AND SUMMARY OF THE INVENTION

It is an object of the invention to provide sustained-release formulations which include an excipient which is useful in a variety of applications, and which may be prepared via wet-granulation or direct compression methods.

It is further an object of the invention to provide sustained-release formulations which include an excipient useful in direct compression methods which has improved compressibility relative to microcrystalline cellulose.

It is further an object of the invention to provide sustained-release formulations which include an excipient which is useful in wet granulation methods which has improved compressibility relative to microcrystalline cellulose.

It is further an object of the invention to provide methods of preparing sustained-release formulations utilizing wet-granulation techniques.

In view of the above objects and others, the present invention is directed to sustained-release formulations comprising an active ingredient, an augmented microcrystalline cellulose which possesses excellent compressibility whether utilized in a direct compression or wet granulation procedure, and a sustained-release carrier. The sustained-release is, e.g. a pharmaceutically acceptable hydrophobic and/or hydrophilic material which can be processed together with the active ingredient and augmented microcrystalline cellulose into a matrix, or can be applied to a core or substrate comprising the active ingredient and the augmented microcrystalline cellulose.

The present invention to is also directed to processes of preparing sustained-release formulations utilizing an augmented microcrystalline cellulose and a sustained-release carrier.

In another embodiment of the invention there is provided sustained-release formulations which include an immediate release core comprising an augmented microcrystalline cellulose and an effective amount of an active agent. The immediate release core is coated with an effective amount of a sustained-release carrier to promote sustained-release of the therapeutic agent. The core may be in the form of, e.g. a compressed tablet.

The invention further relates to a method of preparing a sustained-release formulation by wet granulating a sustained-release carrier, an augmented microcrystalline cellulose and an active agent to obtain a wet mass, drying the wet mass to obtain an agglomerated particulate, and dividing the agglomerated particulate into unit doses comprising a therapeutically effective amount of the active agent. The unit dose may then be, e.g. preferably compressed to form a tablet, or encapsulated in a hard gelatin capsule to make a desired sustained-release dosage form.

In another embodiment of the invention, there is provided a method of preparng a sustained-release dosage form by preparing an immediate release tablet core by wet-granulating an augmented microcrystalline cellulose together with an effective amount of a therapeutic agent and compressing the resultant mixture to form the immediate release core and coating the core with an effective amount of a sustained-release carrier to promote sustained-release of the therapeutic agent.

DETAILED DESCRIPTION OF THE INVENTION

Excipients of the present invention comprise Microcrystalline Cellulose (MCC) and augmenting agents. Microcrystalline cellulose is a well-known tablet diluent, binder and disintegrant. Its chief advantage over other excipients is that it can be directly compressed into self-binding tablets which disintegrate rapidly when placed into water. This widely-used ingredient is prepared by partially depolymerizing cellulose obtained as a pulp from fibrous plant material with dilute mineral acid solutions. Following hydrolysis, the hydrocellulose thereby obtained is purified via filtration and an aqueous slurry is spray dried to form dry, white odorless, tasteless crystalline powder of porous particles of various sizes. Another method of preparing microcrystalline cellulose is disclosed in U.S. Pat. No. 3,141,875. This reference discloses subjecting cellulose to the hydrolytic action of hydrochloric acid at boiling temperatures so that amorphous cellulosic material can be removed and aggregates of crystalline cellulose are formed. The aggregates are collected by filtration, washed with water and aqueous ammonia and disintegrated into small fragments, often called cellulose crystallites by vigorous mechanical means such as a blender. Microcrystalline cellulose is commercially available in several grades which range in average particle size from 20 to 200 microns.

Microcrystalline cellulose is water-insoluble, but the material has the ability to draw fluid into a tablet by capillary action. The tablets then swell on contact and the microcrystalline cellulose thus acts as a disintegrating agent. The material has sufficient self-lubricating qualities so as to allow a lower level of lubricant as compared to other excipients.

Typically, microcrystalline cellulose has an apparent density of about 0.28 $g/cm^3$ and a tap density of about 0.43 $g/cm^3$. *Handbook of Pharmaceutical Excipients*, pages 53–55.

When utilized in pharmaceutical applications, microcrystalline cellulose is typically used as a tablet binder/diluent in wet granulation and direct compression formulations in amounts of 3–30% of the formulation, or more. However, it is known to use more or less microcrystalline cellulose in pharmaceutical products, depending upon the requirements of the formulation.

The novel excipients of the present invention also include one or more compressibility augmenting agents. The compressibility augmenting agent(s) is present in amounts ranging from about 0.1% to about 50% by weight of microcrystalline cellulose.

Direct compression tablet manufacturing is preferred for many products in the pharmaceutical industry. It is a simple process involving less extensive equipment, operating time and cost. Microcrystalline cellulose is a good excipient for direct compression processing. Microcrystalline cellulose has inherently high compactibility due to its plastic deformation and limited elastic recovery. Microcrystalline cellulose usually provides for good drug dispersion, even ordered mixing with some drugs and particular grades of microcrystalline cellulose. However, the material flow properties are relatively poor for most grades of microcrystalline cellulose. Intermittent and non-uniform flow can occur as the formulation moves from the hopper to the die on a tablet press. This non-uniform flow can lead to drug content variations in the finished tableted dosage form.

The popularity of the wet granulation process as compared to the direct compression process is based on at least three potential advantages. First, wet granulation may provide the material to be compacted with a more hydrophilic nature, in order to improve the wetting, disintegration and dissolution characteristics of some hydrophobic drugs or ingredients. Second, the content uniformity and drug segregation-resistance can be enhanced using a granulation step to lock drug and excipient components together during blending. Finally, the micrometric characteristics of the component powders can be optimized prior to compaction, which is often aided by incorporation of a polymeric binder. It is normally considered that this last property imbued by wet granulation will yield a significantly more compactible product and consequently stronger, more robust tablets. However, it has been found that the most compactable tableting excipient, microcrystalline cellulose, can lose between 30 and 50% of its tablet strength enhancing characteristics, following wet granulation. Microcrystalline cellulose tablet weakening caused by wet granulation is observed in all cases where water is added, although the magnitude of loss of compactibility is directed related to the concentration of water used, as well as granulation and drying energetics. This loss of compactibility can result in a very significant loss of functionality, generally leading to a requirement for a larger binder concentration in the formulation and consequently less efficient and more costly tablet production as well as larger tablets.

We have found that the reduction in compactibility of microcrystalline cellulose which has been wet granulated is generally accompanied by a decrease in particle porosity, specific surface area available to adsorb nitrogen and also an increase in granule bulk density and friability. However, granule particle size distribution was found to have a relatively minor effect on granule compactibility. Wet granulation has been found to have only a minor effect on the solubility parameters of microcrystalline cellulose. Further, wet granulation does not alter the X-ray diffraction pattern and the Raman and 13C-NMR spectra of microcrystalline cellulose. However, as a result of granulation, the infrared spectra of microcrystalline cellulose obtained using the techniques of attenuated total reflectance (ATRIR) and optical IR spectroscopy were altered slightly. This is hypothesized to indicate that only the near-surface molecular layers may be significantly involved in interactions with water. Granule properties, including compactibility, have also been found to be influenced by the amount of granulating fluid employed, the duration and rate of wet mass agitation, wet mass storage time before drying, and granule drying technique. Further, granule dewatering by solvent exchange was found to have a beneficial effect on granule compactibility.

It is hypothesized that the granulation-reduced microcrystalline cellulose compactibility is caused at least in significant part by increasing intraparticle and/or interparticle hydrogen bonding. For purposes of the present invention, this phenomenon is termed "quasi-hornification" since, unlike hornification of cellulose fibers described in the literature elsewhere, quasi-hornification of microcrystalline cellulose has not ben observed by us to reduce the ability of microcrystalline cellulose to absorb water vapor. Furthermore, quasi-hornified microcrystalline cellulose was found to be fully reversible, unlike the hornification which occurs when cellulose is wetted. Microcalorimetry indicates that during adsorption of water vapor by granulated microcrystalline cellulose, the extent of intraparticle bond disruption is greater than occurring during water vapor adsorption by ungraduated microcrystalline cellulose. This provides evidence to support the theory that granulation results in increased intraparticle hydrogen bonding, some of which is reversible on adsorption of water vapor.

The present invention is directed in part to a novel agglomerated microcrystalline cellulose excipient which comprises a combination of microcrystalline cellulose as described above together in intimate association with a compressibility augmenting agent. The novel agglomerated microcrystalline cellulose excipient is prepared in a manner which significantly reduces the hydrogen bonding between inter- and/or intra-molecular cellulose-to-cellulose bonding which occurs when regular, commercial grade microcrystalline cellulose is exposed to moisture (water). This can be accomplished, e.g., by preparing an aqueous slurry of microcrystalline cellulose, compressibility augmenting agent(s), and other optional ingredients, and drying the mixture in a manner which inhibits quasi-hornification.

The novel agglomerated microcrystalline cellulose excipient utilizes a compressibility augmenting agent which:
(i) physically restricts the proximity of the interface between adjacent cellulose surfaces;

(ii) inhibits interactions between adjacent cellulose surfaces, for example, via the creation of a hydrophobic boundary at cellulose surfaces; or (iii) accomplishes both (i) and (ii) above.

In one preferred embodiment of the invention, the compressibility augmenting agent which provides a physical barrier between adjacent cellulose surfaces is a silicon dioxide. Silicon dioxide is obtained by insolubilizing dissolved silica in sodium silicate solution. When obtained by the addition of sodium silicate to a mineral acid, the product is termed silica gel. When obtained by the destabilization of a solution of sodium silicate in such a manner as to yield very fine particles, the product is termed precipitated silica. Silicon dioxide is insoluble in water. Prior to the present invention, silicon dioxide, and in particular colloidal silicon dioxide, was used mainly as a glidant and anti-adherent in tableting processes and encapsulation, promoting the flowability of the granulation. The amount of silicon dioxide included in such tablets for those applications is very limited, 0.1–0.5% by weight. Handbook of Pharmaceutical Excipients, ©1986 American Pharmaceutical Association, page 255. This is due in part to the fact that increasing the amount of silicon dioxide in the mixture to be tableted causes the mixture to flow too well, causing a phenomena known to those skilled in the tableting art as "flooding". If the mixture flows too well, a varying tablet weight with uneven content uniformity can result.

Those skilled in the art will appreciate that the name and/or method of preparation of the silicon dioxide utilized in the present invention is not determinative of the usefulness of the product. Rather, as previously mentioned, it has been surprisingly discovered that it is the physical characteristics of the silicon dioxide that are critical. In particular, it has been discovered that silicon dioxide having a relatively large particle size (and correspondingly small surface area), such as silica gel, is not useful in the preparation of the improved microcrystalline cellulose products of the invention. The appended claims are deemed to encompass all forms of silicon dioxide having an average primary particle size from about 1 nm to about 100 µm, and/or a surface area from about 10 $m^2$/g to about 500 $m^2$/g.

The silicon dioxide utilized in the invention is of the very fine particle size variety. In the more preferred embodiments of the invention, the silicon dioxide utilized is a colloidal silicon dioxide. Colloidal silicon dioxide is a submicron fumed silica prepared by the vapor-phase hydrolysis (e.g., at 1110° C.) of a silicon compound, such as silicon tetrachloride. The product itself is a submicron, fluffy, light, loose, bluish-white, odorless and tasteless amorphous powder which is commercially available from a number of sources, including Cabot Corporation (under the tradename Cab-O-Sil); Degussa, Inc. (under the tradename Aerosil); E. I. DuPont & Co.; and W. R. Grace & Co. Colloidal silicon dioxide is also known as colloidal silica, fumed silica, light anhydrous silicic acid, silicic anhydride, and silicon dioxide fumed, among others. A variety of commercial grades of colloidal silicon dioxide are produced by varying the manufacturing process. These modifications do not affect the silica content, specific gravity, refractive index, color or amorphous form. However, these modifications are known to change the particle size, surface areas, and bulk densities of the colloidal silicon dioxide products.

The surface area of the preferred class of silicon dioxides utilized in the invention ranges from about 50 $m^2$/gm to about 500 $m^2$/gm. The average primary particle diameter of the preferred class of silicon dioxides utilized in the invention ranges from about 5 nm to about 50 nm. However, in commercial colloidal silicon dioxide products, these particles are agglomerated or aggregated to varying extents. The bulk density of the preferred class of silicon dioxides utilized in the invention ranges from about 20 g/l to about 100 g/l.

Commercially available colloidal silicon dioxide products have, for example, a BET surface area ranging from about 50±15 $m^2$/gm (Aerosil OX50) to about 400±20 (Cab-O-Sil S-17) or 390±40 $m^2$/gm (Cab-O-Sil EH-5). Commercially available particle sizes range from a nominal particle diameter of 7 nm (e.g., Cab-O-Sil S-17 or Cab-O-Sil EH-5) to an average primary particle size of 40 nm (Aerosil OX50). The density of these products range from 72.0±8 g/l (Cab-O-Sil S47) to 36.8 g/l (e.g., Cab-O-Sil M-5). The pH of the these products at 4% aqueous dispersion ranges from pH 3.5–4.5. These commercially available products are described for exemplification purposes of acceptable properties of the preferred class of silicon dioxides only, and this description is not meant to limit the scope of the invention in any manner whatsoever.

When the novel excipient of the invention utilizes a colloidal silicon dioxide, it has been found that the resultant excipient product surprisingly provides a compressibility which is substantially improved in preferred embodiments even in comparison to the compressibility of normal "off-the-shelf" commercially available microcrystalline cellulose used in direct compression techniques.

In other embodiments of the present invention, it has been discovered that the compressibility of microcrystalline cellulose which is wet granulated is significantly improved by a wider range of silicon dioxide products. Thus, in embodiments of the present invention where an improvement in overall compressibility of the microcrystalline cellulose (whether utilized in wet granulation or dry granulation) is not important, and the microcrystalline cellulose product is to be subjected to wet granulation, it has been discovered that the surface area of the silicon dioxide can be as low as about 50 $m^2$/gm and the average primary particle diameter can be as large as about 100 μm. Such silicon dioxide products are also deemed to be encompassed within the scope of the invention.

The coprocessed product consists of microcrystalline cellulose and silicon dioxide in intimate association with each other. Magnifications of the resultant particles indicate that the silicon dioxide is integrated with, or partially coats, the surfaces of the microcrystalline cellulose particles. When the amount of silicon dioxide included in the excipient is greater than about 20% by weight relative to the microcrystalline cellulose, the silicon dioxide appears to substantially coat the surfaces of the microcrystalline cellulose particles. The exact relationship of the two ingredients of the excipients after coprocessing is not presently understood; however, for purposes of description the coprocessed particles are described herein as including an agglomerate of microcrystalline cellulose and silicon dioxide in intimate association with each other. The coprocessed particles are not necessarily uniform or homogeneous. Rather, under magnification, e.g., scanning electron microscope at 500×, the silicon dioxide at the preferred percent inclusion appears to be an "edge-coating".

Depending upon the amount and type of drying, the concentration of the microcrystalline cellulose and silicon dioxide in the suspension, the novel compressible particles will have different particle sizes, densities, pH, moisture content, etc.

The particulate coprocessed product of this aspect of the present invention possesses desirable performance attributes that are not present when the combination of microcrystalline cellulose and silicon dioxide are combined as a dry mixture. It is believed that the beneficial result obtained by the combination of these two materials is due to the fact that the two materials are intimately associated with each other.

One skilled in the art will appreciate that other classes of compounds having size, surface area, and other similar physical characteristics to silicon dioxide may be useful in physically forming a barrier which may reduce the surface-to-surface interactions (including hydrogen-bonding) between cellulose surfaces. Such materials include (but are not limited to) non-silicon metal oxides. Such obvious modifications of the present invention are deemed to be within the contemplated scope of the appended claims.

In other preferred embodiments of the invention, the compressibility augmenting agent is a material which inhibits interactions between adjacent cellulose surfaces, for example, via the creation of a hydrophobic boundary or barrier at cellulose surfaces. As previously mentioned, compressibility augmenting agents which inhibit surface-to-surface interactions between surfaces of the microcrystalline cellulose include any material which has the ability, via a portion of the molecule, to bind or interact with the surface of the microcrystalline cellulose and at the same time, via another portion of the molecule, to inhibit the attraction of the cellulose surfaces, e.g., via a hydrophobic portion or "tail". Suitable compressibility augmenting agents will have an HLB value of at least 10, preferably at least about 15, and more preferably from about 15 to about 40 or greater. Compressibility augmenting agents having an HLB value from about 30 to about 40 or greater is most preferred.

Surfactants which may be used in the present invention as a compressibility augmenting agent generally include all pharmaceutically-acceptable surfactants, with the proviso that the surfactant have an HLB value of at least 10, and preferably at least about 15.

In certain preferred embodiments, the HLB value of the surfactant is from about 15 to 50, and in further embodiments is most preferably from about 15.6 to about 40. Suitable pharmaceutically-acceptable anionic surfactants include, for example, those containing carboxylate, sulfonate, and sulfate ions. Those containing carboxylate ions are sometimes referred to as soaps and are generally prepared by saponification of natural fatty acid glycerides in alkaline solutions. The most common cations associated with these surfactants are sodium, potassium, ammonium and triethanolamine. The chain length of the fatty acids range from 12 to 18. Although a large number of alkyl sulfates are available as surfactants, one particularly preferred surfactant is sodium lauryl sulfate, which has an HLB value of about 40.

In the pharmaceutical arts, sodium lauryl sulfate has been used as an emulsifying agent in amounts of up to about 0.1% by weight of the formulation. However. surfactants such as sodium lauryl sulfate have been included in coprocessed microcrystalline cellulose compositions. Moreover, surfactants have been used in the amounts described herein to improve the compressibility of microcrystalline cellulose especially in wet granulations. Sodium lauryl sulfate is a water-soluble salt, produced as a white or cream powder, crystals, or flakes and is used as a wetting agent and detergent. Also known as dodecyl sodium sulfate, sodium lauryl sulfate is actually a mixture of sodium alkyl sulfates consisting chiefly of sodium lauryl sulfate. Sodium lauryl sulfate is also known as sulfuric acid monododecyl ester sodium salt. Furthermore, sodium lauryl sulfate is readily available from commercial sources such as Sigma or Aldrich in both solid form and as a solution. The solubility of sodium lauryl sulfate is about 1 gm per 10 ml/water. The fatty acids of coconut oil, consisting chiefly of lauric acid, are catalytically hydrogenated to form the corresponding alcohols. The alcohols are then esterified with sulfuric acid (sulfated) and the resulting mixture of alkyl bisulfates (alkyl sulfuric acids) is converted into sodium salts by reacting with alkali under controlled conditions of pH.

Alternative anionic surfactants include docusate salts such as the sodium salt thereof. Other suitable anionic surfactants include. without limitation, alkyl carboxylates, acyl lactylates, alkyl ether carboxylates, N-acyl sarcosinates, polyvalent alkyl carbonates, N-acyl glutamates, fatty acid, polypeptide condensates and sulfuric acid esters.

In other aspects of the invention amphoteric (amphipathiclamphiphilic surfactants), non-ionic surfactants and/or cationic surfactants are included in the coprocessed compositions of the invention. Suitable pharmaceutically-acceptable non-ionic surfactants such as, for example, polyoxyethylene compounds, lecithin, ethoxylated alcohols, ethoxylated esters, ethoxylated amides, polyoxypropylene compounds, propoxylated alcohols, ethoxylated/propoxylated block polymers, propoxylated esters, alkanolamides, amine oxides, fatty acid esters of polyhydric alcohols, ethylene glycol esters, diethylene glycol esters, propylene glycol esters, glycerol esters, polyglycerol fatty acid esters, SPAN's (e.g., sorbitan esters), TWEEN's (i.e., sucrose esters), glucose (dextrose) esters and simethicone. The HLB for one acceptable non-ionic surfactant, polysorbate 40, is about 15.6.

Other suitable pharmaceutically-acceptable surfactants include acacia, benzalkonium chloride, cholesterol, emulsifying wax, glycerol monostearate, lanolin alcohols, lecithin, poloxamer, polyoxyethylene, and castor oil derivatives.

Those skilled in the art will further appreciate that the name and/or method of preparation of the surfactant utilized in the present invention is not determinative of the usefulness of the product. Rather, as previously mentioned, it has been surprisingly discovered that it is the physical characteristics of surfactants, especially those of the anionic class such as sodium lauryl sulfate, which are critical. In particular, it has been discovered that when an anionic surfactant such as sodium lauryl sulfate is coprocessed with microcrystalline cellulose in the amounts described herein, improved microcrystalline cellulose products of the invention result.

When the novel excipient of the invention utilizes an anionic surfactant, it has been found that the resultant excipient product surprisingly provides a compressibility which is substantially improved in preferred embodiments even in comparison to the compressibility of normal "off-the-shelf" commercially available microcrystalline cellulose used in direct compression techniques. In other embodiments of the present invention, it has been discovered that the compressibility of microcrystalline cellulose which is wet granulated is significantly improved by coprocessing the microcrystalline cellulose with an anionic surfactant such as sodium lauryl sulfate.

Since microcrystalline cellulose is substantially water insoluble, the particle size of this ingredient in the well-dispersed aqueous slurry is directly related to its particle size as it was introduced into the aqueous solution. Most surfactants, on the other hand, tend to be water soluble. Sodium lauryl sulfate, for example, is relatively soluble in water (1 g/10 ml) and, therefore, dissolves in the aqueous slurry. It should be understood, however, that the coprocessed products of the present invention are not solely limited to those which contain a dissolved surfactant. The contemplated compositions can also be prepared from slurries which contain a dispersion of the surfactant as well as the microcrystalline cellulose.

Highly polar molecules having the requisite HLB value range set forth above may also be utilized as the compressibility augmenting agent. Such highly polar molecules include certain dyes, particular those which may be capable of binding to the cellulose surface while thereafter creating a relatively hydrophobic environment due to the presence of a hydrophobic portion of the molecule (e.g., a hydrophobic tail) which "points away" from the cellulose surface and discourages hydrophilic surface-to-surface cellulose interactions, such as hydrogen-bonding. Preferably, the dye is one which is pharmaceutically acceptable for inclusion in solid dosage forms.

Examples of suitable dyes include Congo Red (chemical name: 3,3'-[[1,1'Biphenyl]-4,4'-diylbis-(azo)]bis[4-amino-1-naphthalenesulfonic acid] disodium salt; FD&C Red No. 40 (also known as "Allura Red") (chemical name: Disodium salt of 6-hydroxy-5[(2-methyl-4-sulfophenyl)azo]-2-naphthalenesulfonic acid); FD&C Yellow No. 5 (common name: tartrazine) (chemical name: 5-oxo-1-(p-sulfophenyl)-4-[(p-sulfophenyl)azo]-2-pyrazoline-3-carboxylic acid, trisodium salt); FD&C Yellow No. 6 (common name: Sunset Yellow FCF) (chemical name: Disodium salt of 1-p-sulphophenylazo-2-naphthol-6-sulfonic acid); Ponceau 4R (chemical name: Trisodium-2-hydroxy-1-(4-sulfonato-1-naphthylazo)naphthalene-6,8-disulfonate); Brown HT (chemical name: Disodium 4,4'-(2,4-dihydroxy-5-hydroxymethyl-3,3-phenylene bisazo)di(napthalene-1-sulfonate)); Brilliant Black BN (Chemical name: Tetrasodium 4-acetamido-5-hyroxy-6-[7-sulfonato-4-(4-sulfonatophenylazo)-1-naphthylazo]naphthalene-1,7-disulfonate); Carmoisine (chemical name: Disodium 4-hydroxy-3-(4-sulfanato-1-naphythylazo)Naphthalene-1-sulfonate); Amaranth (chemical name: Trisodium 2-hydroxy-1-(4-sulfonato-1-naphthylazo)naphthalene-3,6-disulfonate); and mixtues thereof.

Other highly polar molecules having the requisite HLB value range set forth above which may be utilized as the compressibility augmenting agent include the active agents themselves. For example, it is well-known to those skilled in the art that certain classes of pharmaceuticals, such as anti-pyschotic drugs, are highly polar in nature and may be utilized as a compressibility augmenting agent in accordance with this invention.

One skilled in the art will appreciate that other classes of highly polar compounds may be useful in reducing the surface-to-surface interactions (including hydrogen-bonding) between cellulose surfaces. Such obvious modifications of the present invention are deemed to be within the contemplated scope of the appended claims.

It is preferred in the present invention that the microcrystalline cellulose and compressibility augmenting agent are coprocessed, resulting in an intimate association of these ingredients, rather than being combined, e.g., as a dry mixture. In preferred embodiments of the present invention, an aqueous slurry of the microcrystalline cellulose, the compressibility augmenting agent(s) and other optional ingredients is prepared in order to obtain (after a drying step) agglomerated particles wherein these components are intimately associated. The aqueous slurry of the microcrystalline cellulose and compressibility augmenting agent are introduced into the spray dryer as a single aqueous medium. However, it is possible to separately introduce each ingredient into separate aqueous medium which are then combined. Other procedures for combining these materials with or without other optional ingredients known to those skilled in the art are deemed to be equivalent to the spray-drying technique described above, and are further deemed to be encompassed by the appended claims.

In preferred embodiments of the present invention, the coprocessing of the microcrystalline cellulose and compressibility augmenting agent is accomplished by forming a well-dispersed aqueous slurry of microcrystalline cellulose in which the compressibility augmenting agent has been dissolved, and thereafter drying the slurry and forming a plurality of microcrystalline cellulose-based excipient particles. Typically, microcrystalline cellulose is first added to an aqueous solution so that a slurry or suspension containing from about 0.5% to about 25% microcrystalline cellulose in the form of solids is obtained. Preferably, the slurry or suspension contains from about 15% to 20% microcrystalline cellulose and most preferably from about 17% to about 19% microcrystalline cellulose. At this stage, it is optionally desirable to adjust the pH of the slurry to about neutral with ammonium hydroxide, sodium hydroxide, and mixtures thereof or the like. The suspension is kept under constant agitation for a sufficient time to assure a uniform distribution of the solids prior to being combined with the compressibility augmenting agent.

For example, silicon dioxide is added to the suspension or slurry in amounts ranging from 0.1% to about 20% by weight, based on the amount of microcrystalline cellulose, amounts from about 0.5% to about 10% are preferred while amounts of from about 1.25% to about 5% by weight are especially preferred. There is no appreciable dissolution of either ingredient (microcrystalline cellulose or silicon dioxide), since both are relatively water insoluble. The microcrystalline cellulose and silicon dioxide are well-dispersed in the slurry or suspension prior to drying and forming the novel particles.

On the other hand, the surfactant is added to the suspension or slurry in amounts ranging from about 0.1% to about 20% by weight, preferably from about 0.1 to about 5% by weight, based on the amount of microcrystalline cellulose, and in certain embodiments preferably from about 0.15% to about 0.4%, by weight. When the surfactant is sodium lauryl sulfate, the amount is most preferably from about 0.2 to about 0.3%, by weight. The surfactant can be added to the suspension as either a solid or in solution form. The microcrystalline cellulose is thus well-dispersed in the slurry or suspension and the surfactant is dissolved therein prior drying and forming the novel particles. It will be understood that other useful surfactants can be used in like amounts or even greater amounts, i.e. up to 20% by weight or even more. The usable concentration range for the selected surfactant depends in part upon not only its molecular weight but also its degree of foaming, particularly when present in agitated slurries which will be spray dried to form the desired particulate. Thus, in those aspects of the invention where surfactants other than sodium lauryl sulfate are coprocessed with the microcrystalline cellulose, it is to be understood that the surfactant will be present in an amount which enhances the compressibility of the microcrystalline cellulose and yet does not have a degree of foaming which would substantially inhibit spray drying.

Other compressibility augmenting agents (including highly polar dyes, highly polar drugs, and other useful materials having a HLB from about 15 to about 50) may be included in the aqueous slurry in amounts ranging from about 0.1% to about 20%, by weight, and more preferably from about 0.5 to about 10%, by weight.

After a uniform mixture of the ingredients is obtained in the suspension, the suspension is dried to provide a plurality of microcrystalline cellulose-based excipient particles having enhanced compressibility (e.g., dried in a manner which inhibits quasi-hornification).

In the (preferred) spray-drying process, the aqueous dispersion of microcrystalline cellulose and surfactant is brought together with a sufficient volume of hot air to produce evaporation and drying of the liquid droplets. The highly dispersed slurry of microcrystalline cellulose and surfactant is pumpable and capable of being atomized. It is sprayed into a current of warm filtered air, which supplies the heat for evaporation and conveys a dried product to a collecting device. The air is then exhausted with the removed moisture. The resultant spray-dried powder particles are approximately spherical in shape and are relatively uniform in size, thereby possessing excellent flowability. The coprocessed product consists of microcrystalline cellulose and surfactant in intimate association with each other. The exact relationship of the two ingredients of the excipients after coprocessing is not presently understood; however, for purposes of description the coprocessed particles are described herein as including an agglomerate of microcrystalline cellulose and surfactant in intimate association with each other. By "intimate associate", it is meant that the surfactant has in some manner been integrated with the microcrystalline cellulose particles, e.g., via a partial coating of the microcrystalline particles, as opposed to a chemical interaction of the two ingredients. The term "intimate association" is therefore deemed for purposes of the present description as being synonymous with "integrated" or "united". The coprocessed particles are not necessarily uniform or homogeneous.

It is preferred that the suspension be dried using spray-drying techniques, as they are known in the art. Other drying techniques, however, such as flash drying, ring drying, micron drying, tray drying, vacuum drying, radio-frequency drying, and possibly microwave drying, may also be used, although spray drying is preferred.

Depending upon the amount and type of drying, the concentration of the microcrystalline cellulose and compressibility augmenting agent in the suspension, the novel compressible particles will have different particle sizes, densities, pH, moisture content, etc.

The particulate coprocessed product of the present invention possesses desirable performance attributes that are not present when the combination of microcrystalline cellulose and compressibility augmenting agent are combined as a dry mixture. It is believed that the beneficial result obtained by the combination of these two materials is due to the fact that the two materials are intimately associated with each other. It has also been found that intimate association of microcrystalline cellulose and other detergent-like materials such as simethicone, even when they are dissolved/dispersed in the aqueous solutions which form the microcrystalline cellulose slurry, fail to provide microcrystalline cellulose with enhanced compressibility.

The average particle size of the agglomerated microcrystalline cellulose excipient of the present invention ranges from about 10 microns to about 1000 microns. Particle sizes of about 10–500 microns are preferred, particle sizes of about 30–250 microns are more preferred and particle sizes of about 40–200 microns are most preferred. It will be appreciated by those of ordinary skill in the art that the drying of the aqueous suspension results in a random size distribution of the novel excipient particles being produced. For example, if spray drying techniques are used, droplet size, temperatures, agitation, dispersion, air flow, atomizer wheel speed, etc. will effect final particle size. Furthermore, it is within the scope of the invention to sort or mechanically alter the dried particles according to ranges of particle sizes depending upon end uses. The particle size of the integrated excipient is not narrowly critical, the important parameter being that the average size of the particle must permit the formation of a directly compressible excipient which forms pharmaceutically acceptable tablets.

The novel agglomerated microcrystalline cellulose excipient has a bulk (loose) density ranging from about 0.2 g/ml to about 0.6 g/ml, and most preferably from about 0.22 g/ml to about 0.55 g/ml. The novel excipient has a tapped density ranging from about 0.20 g/ml to about 0.70 g/ml, and most preferably from about 0.35 g/ml to about 0.60 g/ml. The pH of the particles is most preferably about neutral, although granulates having a pH of from about 3.0 to about 8.5 are possible. The moisture content of the excipient particles will broadly range from about 0.5% to about 15%, preferably from about 2.5% to about 6%, and most preferably from about 3.0% to about 5% by weight.

The angle of repose is a measurement used to determine the flow characteristics of a powder. The angle of repose is subject to experiment and experimenter, but in a comparative test, the novel excipient is superior.

The novel agglomerated microcrystalline cellulose excipient of the invention is free-flowing and directly compressible. Accordingly, the excipient may be mixed in the desired proportion with an active agent and optional lubricant (dry granulation), and then directly compressed into solid dosage forms. In preferred embodiments of the present invention wherein the surfactant is sodium lauryl sulfate, the novel excipient represents an augmented microcrystalline cellulose having improved compressibility as compared to standard commercially available grades of microcrystalline cellulose.

Alternatively, all or part of the excipient may be subjected to a wet granulation with the active ingredient. A representative wet granulation includes loading the novel excipient particles into a suitable granulator, such as those available from Baker-Perkins, and granulating the particles together with the active ingredient, preferably using an aqueous granulating liquid. The granulating liquid is added to the mixture with stirring until the powdery mass has the consistency of damp snow and then wet screened through a desired mesh screen, for example, having a mesh from about 12 to about 16. The screened granulate is then dried, using standard drying apparatus such as a convection oven before undergoing a final screening. Additional dry screening of this material is possible, such as by using screens of from about 40 to about 200 mesh. Those materials flowing through 40 and 60 mesh screens may be firher ground prior to ultimate tablet formulation. The thus obtained granulate containing the novel excipient is now capable of undergoing tableting or otherwise placed into a unit dosage form.

In certain preferred embodiments, a portion of the total amount of the novel excipient is wet granulated with the active ingredient, and thereafter the additional portion of the novel excipient is added to the granulate. In yet other embodiments, the additional portion of the novel excipient to be added to the excipient/active ingredient granulate may be substituted with conventional microcrystalline cellulose, or other excipients commonly used by those skilled in the art, depending of course upon the requirements of the particular formulation.

By virtue of the novel excipient of the present invention, the amount of the novel excipient compared to the amount of microcrystalline cellulose which must be used in a wet granulation technique to obtain an acceptable solid dosage form is substantially reduced.

In other embodiments of the invention, a further material is added to the aqueous slurry of microcrystalline cellulose and compressibility augmenting. Such additional materials include silicon dioxides, non-silicon metal oxides, starches, starch derivatives, surfactants, polyalkylene oxides, cellulose ethers, celluloses esters, mixtures thereof, and the like. Specific further materials which may be included in the aqueous slurry (and consequently in the resultant agglomerated microcrystalline cellulose excipient) are aluminum oxide, stearic acid, kaolin, polydimethylsiloxane, silica gel, titanium dioxide, diatomaceous earth, corn starch, high amylose corn starch, high amylopectin corn starch, sodium starch glycolate, hydroxylated starch, modified potato starch, mixtures thereof, and the like. These additives may be included in desired amounts which will be apparent to those skilled in the art.

In addition to one or more active ingredients, additional pharmaceutically acceptable excipients (in the case of pharmaceuticals) or other additives known to those skilled in the art (for non-pharmaceutical applications) can be added to the novel excipient prior to preparation of the final product. For example, if desired, any generally accepted soluble or insoluble inert pharmaceutical filler (diluent) material can be included in the final product (e.g., a solid dosage form). Preferably, the inert pharmaceutical filler comprises a monosaccharide, a disaccharide, a polyhydric alcohol, inorganic phosphates, sulfates or carbonates, and/or mixtures thereof. Examples of suitable inert pharmaceutical fillers include sucrose, dextrose, lactose, xylitol, fructose, sorbitol, calcium phosphate, calcium sulfate, calcium carbonate, "off-the-shelf" microcrystalline cellulose, mixtures thereof, and the like.

An effective amount of any generally accepted pharmaceutical lubricant, including the calcium or magnesium soaps may optionally be added to the novel excipient at the time the medicament is added, or in any event prior to compression into a solid dosage form. The lubricant may comprise, for example, magnesium stearate in any amount of about 0.5–3% by weight of the solid dosage form. In embodiments where a surfactant is included as part or all of the compressibility augmenting agent, an additional inclusion lubricant may not be necessary.

SUSTAINED-RELEASE CARRIER

Matrix Formulations

In one embodiment of the invention, the sustained-release carrier is incorporated in a sustained-release matrix to impart sustained-release of the active agent from the final formulation. The sustained release carrier may be hydrophobic or hydrophilic. Suitable materials which may be included in the sustained release carrier of the present invention include alkylcelluloses such as natural or synthetic celluloses derivatives (e.g. ethylcellulose), acrylic and methacrylic acid polymers and copolymers, zein, and mixtures thereof.

In another embodiment, suitable biocompatible, preferably biodegradable polymers can be utilized as the sustained release carrier. The biodegradable polymeric material may comprise a polylactide, a polyglycolide, a poly(lactide-co-glycolide), a polyanhydride, a polyorthoester, polycaprolactones, polyphosphazenes, polysaccharides, proteinaceous polymers, soluble derivatives of polysaccharides, soluble derivatives of proteinaceous polymers, polypeptides, polyesters, and polyorthoesters.

The polysaccharides may be poly-1,4-glucans, e.g., starch glycogen, amylose, amylopectin, and mixtures thereof. The biodegradable hydrophilic or hydrophobic polymer may be a water-soluble derivative of a poly-1,4-glucan, including hydrolyzed arnylopectin, hydroxyalkyl derivatives of hydrolyzed amylopectin such as hydroxyethyl starch (HES), hydroxyethyl amylose, dialdehyde starch, and the like.

In yet other preferred embodiments, sustained-release of the active agent is accomplished via a sustained release carrier comprising a synthetic or naturally occurring gum. Examples of naturally occurring gums include, e.g., the heteropolysaccharides and homopolysaccharides. An especially preferred heteropolysaccharide is xanthan gum, which is a high molecular weight (>$10^6$) heteropolysaccharide. Other preferred heteropolysaccharides include derivatives of xanthan gum, such as deacylated xanthan gum, the carboxymethyl ether, and the propylene glycol ester.

The homopolysaccharides useful in the present invention include galactomannan gums, which are polysaccharides composed solely of mannose and galactose. Preferred galactomannan gums are those which are capable of cross-linking with the heteropolysaccharide. In particular, galactomannans which have higher proportions of unsubstituted mannose regions have been found to achieve more interaction with the heteropolysaccharide when exposed to an environmental fluid. Locust bean gum, which has a higher ratio of mannose to galactose, is especially preferred as compared to other galactomannans such as guar and hydroxypropyl guar.

Other natural or synthetic gums known to those skilled in the food and pharmaceutical arts are also useful as the controlled release carrier of the invention. Such gums include alginic acid derivatives, carageenan, tragacanth, acacia, karaya, guar gum, agar, acacia, galactans, mannans, and the like.

Water swellable polymers may be used in addition to or instead of gums to promote sustained-release of the active agent from the final formulation. Such water swellable polymers include cellulose ethers, carboxyvinyl polymer and the like.

The combination of xanthan gum with locust bean gum is an especially preferred gum combination. In certain embodiments, the controlled release properties of the sustained-release carrier are optimized when the ratio of heteropolysaccharide gum to galactomannan gum is from about 3:1 to about 1:3, and most preferably about 1:1. However, in this embodiment, the sustained release carrier of the invention may comprise from about 1% to about 99% by weight heteropolysaccharide gum and from about 99% to about 1% by weight homopolysaccharide gum.

Optionally, the sustained-release carrier includes a release modifying agent. A release modifying agent according to the invention includes any pharmaceutically acceptable substance which my alter, e.g. prolong or increase, the release rate of the active agent form the formulation upon exposure to an aqueous environment, e.g. gastric fluid or dissolution medium. Suitable release modifying agents which may be incorporated into the matrix formulations of the present invention include, e.g., monovalent or multivalent metal cations. Preferably, the salts are inorganic salts, including e.g., alkali metal and/or alkaline earth metal sulfates, chlorides, borates, bromides, citrates, acetates, lactates, etc. In particular, these salts include, e.g., calcium sulfate, sodium chloride, potassium sulfate, sodium carbonate, lithium chloride, tripotassium phosphate, sodium borate, potassium bromide, potassium fluoride, sodium bicarbonate, calcium chloride, magnesium chloride, sodium citrate, sodium acetate, calcium lactate, magnesium sulfate and sodium fluoride. Multivalent metal cations may also be utilized. In preferred embodiments, the release modifying agents are bivalent. Particularly preferred salts are calcium sulfate and sodium chloride.

In those embodiments including a release modifying agent any effective amount may be employed. Preferably, the release modifying agent is included in an amount ranging from about 1 to about 20% by weight of a sustained-release carrier comprising xanthan gum and locust bean gum.

Other release modifying agents include sugars, e.g. sucrose, starches, water-soluble alkylcellulose derivatives such as hydroxypropylmethylcellulose, urea, and the like.

Mixtures of any of the foregoing, and other pharmaceutically acceptable release retardants or release modifying agents known to those skilled in the art may also be used in accordance with the present invention.

The final sustained-release oral dosage form may contain from about 1 to about 99% (by weight) of sustained release carrier. Preferably, the weight percent of the sustained release carrier ranges from about 1 to about 80%.

In certain preferred embodiments of the present invention, the sustained release carrier is a pharmaceutically acceptable acrylic polymer, including but not limited to acrylic acid and methacrylic acid copolymers, methyl methacrylate, methyl methacrylate copolymers, ethoxyethyl methacrylates, cynaoethyl methacrylate, aminoalkyl methacrylate copolymer, poly(acrylic acid), poly(methacrylic acid), methacrylic acid alkylamine copolymer, poly(methyl methacrylate), poly (methacrylic acid)(anhydride), polymethacrylate, polyacrylamide, poly(methacrylic acid anhydride), and glycidyl methacrylate copolymers. In other embodiments, the sustained-release carrier may further include a relatively hydrophilic material, including but not limited to materials such as hydroxyalkylcelluloses such as hydroxypropylmethylcellulose and mixtures of the foregoing.

A pharmaceutically acceptable plasticizer may also optionally be included in the sustained-release carrier of the present invention. A non-limiting list of plasticizers includes include water insoluble plasticizers such as dibutyl sebacate, diethyl phthalate, triethyl citrate, tributyl citrate, and triacetin, although it is possible that other water-insoluble plasticizers (such as acetylated monoglycerides, phthalate esters, castor oil, etc.) may be used. Triethyl citrate is an especially preferred plasticizer.

In addition to the above ingredients, a sustained-release carrier may also include suitable quantities of pharmaceutical adjuvants, e.g., diluents, lubricants, binders, granulating aids, colorants, flavorants and glidants that are conventional in the pharmaceutical art. A non-limiting list of suitable adjuvants include spray dried lactose, polyvinylpyrolidone (PVP), talc, magnesium stearate, and mixtures thereof. The quantities of these additional materials will be sufficient to provide the desired effect to the desired formulation. The sustained-release carrier may contain up to about 50% by weight of pharmaceutical adjuvant(s).

Other examples of pharmaceutically acceptable carriers and excipients that may be used to formulate oral dosage forms are described in the *Handbook of Pharmaceutical Excipients*, American Pharmaceutical Association (1986), incorporated by reference in its entirety.

Of course, any of the release retardants mentioned hereinabove may be utilized in any mixture or combination, either as a homogeneous combination or in the form of a heterogeneous combination, e.g., as part of a layered formulation.

The sustained-release profile of the matrix formulations of the invention can be altered, for example, by varying the amount of retardant, e.g., hydrophobic polymer, by varying the amount of plasticizer relative to hydrophobic polymer, by the inclusion of additional ingredients or excipients, by altering the method of manufacture, etc.

The sustained-release matrix according to the invention provides sustained-release of the active agent for a period of, e.g. about 8 to about 24 hours or more.

Sustained-release carrier formulations, e.g., matrix formulations, may be prepared in accordance with the present invention using any art-known techniques. The sustained-release carrier formulations may be prepared, e.g., melt-granulation, wet granulation, melt-extrusion, dry blending, wet-extrusion, or by other art-known techniques.

In preferred embodiments of the invention, the sustained-release matrix is prepared by wet-granulating the requisite amounts of sustained-release carrier and augmented microcrystalline cellulose to form a moistened mass. Preferably, the sustained-release carrier and augmented microcrystalline cellulose are in powder form. The moistened mass is then screened and dried, e.g. using a fluid bed dryer. The dried granulate may then be further screened to obtain a granulate within a desired uniform particle size. The dried granulate may then be divided into unit doses and encapsulated in a hard gelatin capsule, or compressed into tablets of desired size and shape.

In other embodiments, a pre-manufactured sustained-release matrix is prepared to which the active agent is added. The mixture is then wet-granulated as described above, and, e.g. compressed to form a tablet. For example, a sustained-release matrix may be prepared by blending a mixture of xanthan gum, locust bean gum and an augmented microcrystalline cellulose in powder form in a granulator, e.g., a high speed mixer. A sufficient amount of water is added to the mixture, which is fater blended. The mixed product, which is now in the form of a wet mass, is removed from the granulator and dried, e.g. in a fluid bed dryer. The dried granulation is screened to produce dried granules within a desired particle size range. The sustained-release excipient is then ready to be used as a sustained release matrix which is suitable for direct compression with any active medicament to form a sustained-release dosage form. Alternatively, the dried screened granules may be encapsulated in hard gelatin capsules to produce the final solid sustained-release dosage form.

Additional pharmaceutical processing aids such as lubricants, e.g. magnesium stearate may be added to the sustained-release carrier or sustained-release excipient prior to further processing.

The active agent may be wet-granulated together with the sustained-release carrier and/or augmented microcrystalline cellulose. The resultant moistened mass is then processed as described above to obtain the desired final dosage form.

In a preferred embodiment, the active agent is added to the augmented microcrystalline cellulose during manufacture of the excipient proper. Then, the requisite amount of augmented microcrystalline cellulose/active agent blend is combined with the sustained-release carrier and further processed to produce the final dosage form.

Any art known technique for preparing the final dosage form may be used in accordance with the present invention.

SUSTAINED-RELEASE COATING FORMULATIONS

The sustained-release coating includes at least one sustained-release carrier, such as described hereinabove. In embodiments of the invention including a sustained-release coating, the immediate release core comprising the augmented microcrystalline cellulose and the active ingredient is coated with a sufficient amount of sustained-release coating to provide sustained-release of the active ingredient, e.g. for up to about 8 to about 24 hours. The amount of sustained-release coating applied to the core is typically in the range of, e.g. a weight gain level from about 2 to about 30 percent, although the overcoat may be greater depending upon the physical properties of the particular active agent utilized and the desired release rate, and other factors known to those skilled in the art.

The sustained-release coating is preferably an aqueous or organic based coating. Preferably, the sustained-release coating includes a hydrophobic or hydrophilic material.

In certain preferred embodiments of the present invention, the sustained-release coating includes a hydrophobic polymer, e.g. a pharmaceutically acceptable acrylic polymer, including but not limited to acrylic acid and methacrylic acid copolymers, methyl methacrylate copolymers, ethoxyethyl methacrylates, cynaoethyl methacrylate, aminoalkyl methacrylate copolymer, poly(acrylic acid), poly(methacrylic acid), methacrylic acid alkylamide copolymer, poly(methyl methacrylate), polymethacrylate, polyacrylamide, aminoalkyl methacrylate copolymer, poly(methacrylic acid anhydride), glycidyl methacrylate copolymers, waxes, fatty acids, shellac, wax-type substances including hydrogentaed castor oil and hydrogenated vegetable oil, synthetic waxes, hydrogenated fats, stearic acid and stearyl alcohol. Examples of suitable commercially available polymethacrylates include Eudragit RS or RL, commercially available from Röhm Tech, Inc.

In other preferred embodiments, the sustained-release coating includes a hydrophobic polymer which is a hydrophobic cellulosic material such as ethylcellulose. Those skilled in the art will appreciate that other cellulosic polymers, including other alkyl cellulosic polymers, may be substituted for part or all of the ethylcellulose included in the hydrophobic polymer coatings of the present invention.

In most preferred embodiments, the sustained release coating is in the form of an aqueous dispersion. One commercially-available aqueous dispersion of ethylcellulose is Aquacoat® (FMC Corp., Philadelphia, Pa., U.S.A.). Another aqueous dispersion of ethylcellulose is commercially available as Surelease® (Colorcon, Inc., West Point, Pa., U.S.A.).

In embodiments of the present invention where the sustained-release coating comprises an aqueous dispersion of a hydrophobic polymer, the inclusion of an effective amount of a plasticizer in the aqueous dispersion of hydrophobic polymer will further improve the physical properties of the film. Generally, the amount of plasticizer included in a coating solution is based on the concentration of the hydrophobic polymer, e.g., most often from about 1 to about 50 percent by weight of the hydrophobic polymer. Concentration of the plasticizer, however, can only be properly determined after careful experimentation with the particular coating solution and method of application.

Examples of suitable plasticizers for ethylcellulose include water insoluble plasticizers such as dibutyl sebacate, diethyl phthalate, triethyl citrate, tributyl citrate, and triacetin, although it is possible that other water-insoluble plasticizers (such as acetylated monoglycerides, phthalate esters, castor oil, etc.) may be used. Triethyl citrate is especially preferred.

The sustained-release profile of the sustained-release formulations of the invention can be altered, for example, by varying the thickness of the sustained-release coating, changing the particular sustained release carrier used, or altering the relative amounts of, e.g., different acrylic resin lacquers, altering the manner in which the plasticizer is added (e.g., when the sustained-release coating is derived from an aqueous dispersion of hydrophobic polymer), by varying the amount of plasticizer relative to hydrophobic polymer, by the inclusion of additional ingredients or excipients, by altering the method of manufacture, etc.

In other embodiments of the present invention, the sustained-release coating includes an enteric coating material in addition to or instead or the hydrophobic polymer coating. Examples of suitable enteric polymers include cellulose acetate phthalate, hydroxypropylmethylcellulose phthalate, polyvinylacetate phthalate, methacrylic acid copolymer, shellac, hydroxypropylmethylcellulose succinate, cellulose acetate trimellitate, and mixtures of any of the foregoing. An example of a suitable commercially available enteric material is available under the trade name Eudragit™ L 100-55.

In further embodiments, the dosage form may be coated with at least an additional coating layer, e.g. a protective and or barrier coat. An example of a suitable material which may be used for such an additional coating layer is hydroxypropylmethylcellulose (e.g., Opadry®, commercially available from Colorcon, West Point, Pa.).

The sustained release or additional coatings may be applied in any pharmaceutically acceptable manner known to those skilled in the art. For example, in one embodiment, the coating is applied via a fluidized bed or in a coating pan. For example, the coated tablets may be dried, e.g., at about 60°–70° C. for about 3–4 hours in a coating pan. The solvent for the sustained-release coating may be organic, aqueous, or a mixture of an organic and an aqueous solvent. The organic solvents may be, e.g., isopropyl alcohol, ethanol, and the like, with or without water.

Any art-known technique may be used to prepare the sustained-release coated dosage forms of the present invention. In one preferred embodiment, simply by way of example, the requisite amounts of active agent and the augmented microcrystalline cellulose are wet granulated to form a moistened mass. The moistened mass is then screened and dried. The dried mass is then compressed to form an immediate release core of desired size and shape, e.g. a tablet.

The immediate release core comprising the active agent and the augmented microcrystalline cellulose is then coated with a sustained-release carrier using any art-known coating process. The resulting sustained-release dosage form may then be dried, e.g. in a fluid bed dryer, if needed.

In preferred embodiments, multiple layers of sustained-release coating may be applied.

Additional coating layers may be applied to the dosage form. Such additional coating layers may be applied prior to or after the application of the sustained-release coating layer(s) as desired. Such additional coating or multiple coating layers may be applied to the immediate release core prior to addition of a sustained-release coat or, alternatively, after coating with the sustained-release coating. Such coating or coatings serve as, e.g. protective and/or barrier functions.

ACTIVE AGENTS

The active agent(s) which may be incorporated with the novel excipient described herein into solid dosage forms invention include systemically active therapeutic agents, locally active therapeutic agents, disinfecting agents, chemical impregnants, cleansing agents, deodorants, fragrances, dyes, animal repellents, insect repellents, fertilizing agents, pesticides, herbicides, fungicides, and plant growth stimulants, and the like.

A wide variety of therapeutic agents can be used in conjunction with the present invention. The therapeutic agents (e.g. pharmaceutical agents) which may be used in the compositions of the present invention include both water soluble and water insoluble drugs. Examples of such therapeutic agents include antihistamines (e.g., dimenhydrinate, diphenhydramine, chlorpheniramine and dexchlorpheniramine maleate), analgesics (e.g., aspirin, codeine, morphine, dihydromorphone, oxycodone, etc.), naproxyn, diclofenac, indomethacin, flurbiprofen, ketoprofen, piroxican, sulindac, anti-emetics (e.g., metoclopramide), anti-epileptics (e.g., phenytoin, meprobamate and nitrazepam), vasodilators (e.g., nifedipine, papaverine, diltiazem and nicardipine), anti-tussive agents and expectorants (e.g., codeine phosphate), anti-asthmatics (e.g. theophylline and aminophylline), antacids, anti-spasmodics (e.g. atropine, scopolamine), antidiabetics (e.g., insulin), diuretics (e.g., ethacrynic acid, bendrofluazide), anti-hypotensives (e.g., propranolol, clonidine), antihypertensives (e.g., clonidine, methyldopa), bronchodilators (e.g., albuterol), steroids (e.g., hydrocortisone, triamcinolone, prednisone), antibiotics (e.g., tetracycline), antihemorrhoidals, hypnotics, psychotropics, antidiarrheals, mucolytics, sedatives, decongestants, laxatives, vitamins, stimulants (including appetite suppressants such as phenylpropanolamine). The above list is not meant to be exclusive.

In preferred embodiments of the invention, the ratio of active agent to sustained-release carrier is from about 1:3 to about 1:7 by weight. In other preferred embodiments, the active agent comprises from about 1 to about 80% by weight of the final formulation.

The sustained-release formulations of the invention may also include other pharmaceutical adjuvants, e.g., flavorants, sweeteners and taste masking agents. Generally any flavoring or food additive such as those described in *Chemicals Used in Food Processing*, pub 1274 by the National Academy of Sciences, pages 63–258 may be used. Generally, the final product may include from about 0.1% to about 5% by weight flavorant.

The sustained-release formulations of the present invention may also contain effective amounts of coloring agents, (e.g., titanium dioxide, F.D. & C. and D. & C. dyes; see the Kirk-Othmer Encyclopedia of Chemical Technology, Vol. 5, pp. 857–884, hereby incorporated by reference), stabilizers, binders, odor controlling agents, and preservatives.

DETAILED DESCRIPTION OF THE PREFERRED EMBODIMENTS

The following examples illustrate various aspects of the present invention. They are not to be construed to limit the claims in any manner whatsoever.

EXAMPLES 1 and 2 PREPARATION OF EXCIPIENT

EXAMPLE 1

MCC-SiO$_2$ Product—5% w/w SiO$_2$

A. EXCIPIENT PARTICLES

In this example, about 6.2 kilograms of microcrystaliine cellulose (MCC), (Mendell Co., Inc. Patterson, N.Y.) in the form of a wet cake was combined with 5.2 kilograms of water in a mix tank to form a slurry containing about 15% solids. The pH was adjusted to about neutral with about 3 ml of ammonium hydroxide. The slurry was allowed to mix for about 15 minutes before being combined with 5% w/w silicon dioxide ($SiO_2$), 200 $m^2$/g (CaboSil, PTG grade, available from Cabot Corp., Tuscola, Ill.) After allowing the materials to become intimately combined, the slurry was spray dried using a Niro Production Minor (Niro, Columbia, Md.), inlet temperature −215° C., outlet temperature −125° C., atomizer wheel speed 22,300 rpm, to provide an augmented MCC-$SiO_2$ excipient having an average particle size of 40–60 microns.

B. GRANULATION OF EXCIPIENT PARTICLES

The MCC-$SiO_2$ particles obtained as a result of step 1A. were wet granulated in a Baker-Perkins 10 liter high-sheer granulator for 3 minutes using water as the granulating fluid. The resultant product was wet screened through a 12 mesh screen, tray dried in a convection oven for about 2–3 hours until a moisture content of less than 5% was obtained, dry screened and sieved to obtain an average particle size of from about 55 to about 70 microns.

EXAMPLE 2

MCC-SLS Product—0.25% w/w SLS

A. EXCIPIENT PARTICLES

In this example, about 6.2 kilograms of microcrystalline cellulose (MCC), (Mendell Co., Inc. Patterson, N.Y.) in the form of a wet cake was combined with 5.2 kilograms of water in a mix tank to form a slurry containing about 15% solids. The pH was adjusted to about neutral with about 3 ml of ammonium hydroxide. The slurry was allowed to mix for about 15 minutes before being combined with 0.25% w/w sodium lauryl sulfate (SLS) powder (available from Spectrum Chemical, Gardena, Calif.) After allowing the materials to become intimately combined, the slurry was spray dried using a Niro Production Minor (niro, Columbia, Md.), inlet temperature−215° C., outlet temperature−125° C., atomizer wheel speed 22,300 rpm, to provide an augmented MCC-SLS excipient having an average particle size of 40–60 microns.

B. GRANULATION OF EXCIPIENT PARTICLES

The MCC-SLS particles obtained as a result of step 1 A. were wet granulated in a Baker-Perkins 10 liter high-sheer granulator for 3 minutes using water as the granulating fluid. The resultant product was wet screened through a 12 mesh screen, tray dried in a convection oven for about 2–3 hours until a moisture content of less than 5% was obtained, dry screened and sieved to obtain an average particle size of from about 55 to about 70 microns.

EXAMPLES 3–22—SUSTAINED-RELEASE FORiMULATIONS

EXAMPLE 3

A controlled release excipient according to the present invention is prepared as follows. First, 630 g of the augmented microcrystalline cellulose excipient of Example 1 and 270 g of a hydrophilic material comprising 135 g of xanthan gum and 135 g of locust bean gum, all in a powder form having an average particle size of less than 50 microns are blended for two minutes in a granulator (i.e., a high speed mixer having a combination chopper/impeller). After pre-mixing, 100 ml of water is added until there is sharp rise in the power consumption (about 2–3 minutes). The mixed product, which is now in the form of granules, is removed from the granulator and dried in a convection air-oven for 24 hours at a temperature of about 40°–60° C. The dried granulation is then passed through a 20 mesh screen. The product is now ready to be granulated with an active, the result of which is suitable for compression to form a sustained-release tablet.

Wet Granulation

Veraparnil HCl is a relatively soluble active ingredient which has a dose of about 240 mg in a sustained-release tablet form. The active ingredient (verapamil) is granulated with the sustained-release carrier as follows. The 385 g of the sustained-release carrier is first blended with 115 g verapamil HCL for two minutes in a granulator. After premixing, about 90 ml of water is added until there is a sharp rise in the power consumed by the granulator (about 2–3 minutes). The mixed product, which is now in the form of granules, is removed from the granulator and dried in a convection air-oven for 24 hours at a temperature of about 40°–60° C. The dried granulation is then passed through a 20 mesh screen. The final composition of the mixture is about 77.0% of the sustained-release carrier and 23.0% of verapamil HCl.

The mixture is blended with hydrogenated vegetable oil for about 5 minutes in a V-blender. Magnesium stearate is then added and the mixture is blended for an additional 4 minutes. The final composition of the mixtures is about 75.0% of the sustained-release carrier, 22.5% verapamil HCl, 2.00% hydrogenated vegetable oil, and 0.500% magnesium stearate, by weight. The mixture is then compressed on a Stokes RB-2 rotary tablet press with sixteen stations. The average weight of the tablets produced is about 1067 mg and the crushing strength about 7–8 kgs. Each tablet contains about 240.08 verapamil, 800.25 mg sustained-release carrier, 21.34 mg hydrogenated vegetable oil, and 5.34 mg magnesium stearate.

EXAMPLE 4

A sustained-release verapamil tablet is prepared in accordance with Example 3, except that the augmented microcrystalline cellulose of Example 2 is used. The resultant tablet provided an in-vitro dissolution profile indicative of a sustained-release verapamil formulation.

EXAMPLE 5

A sustained-release verapamil tablet is prepared in accordance with Example 5, a 50:50 blend of the excipients of Examples 1 and 2 are used. The resultant tablet produced an in-vitro dissolution profile indicative of a sustained-release verapamil formulation.

EXAMPLE 6

A sustained-release carrier according to the present invention is prepared as follows. First 600 g of the excipient of Example 1 and 300 g of a mixture of xanthan gum and locust bean gum in approximately a 1:1 ratio, all in powder form having an average particle size of less than about 50 microns, are blended for two minutes in a granulator (i.e., a high speed mixer having a combination chopper/impeller). About 125 ml of water is added to the mixture until there is a sharp rise in the power consumed (about 2–3 rminutes). The mixed product, which is now in the form of granules, is removed from the granulator and dried in a convection air-oven for 24 hours at a temperature of about 40°–60° C. The dried granulation is then passed through a 20 mesh screen. The product is now ready to be used as a slow release carrier which is suitable for direct compression with any active medicament to form a sustained-release tablet.

Sustained-release tablets according to the present invention are prepared as follows. The sustained-release carrier as prepared above is first blended with chlorpheniramine maleate for 10 minutes in a V-blender. Magnesium stearate is then added as a lubricant and the mixture is blended for an additional 5 minutes. The final composition of the mixture is about 87.5% of the sustained-release carrier, 12% chlorpheniramine maleate, and 0.5% magnesium stearate by weight.

The mixture is then compressed on a Stokes RB-2 rotary tablet press with sixteen stations, the target weight of the tablets being 100 mg and the crushing strength about 6–8 kgs.

EXAMPLE 7

In this example, sustained-release tablets are prepared in accordance with the procedure set forth in Example 6 above, except that 600 mg of the excipient of Example 2 is used. The resultant tablets produced an in-vitro dissolution profile indicative of a sustained release chlorpheniramine formulation.

EXAMPLE 8

In this example, sustained-release tablets are prepared in accordance with the procedure set forth in Example 6 above, except that a combination of 300 mg of the excipient of Example 1 and 300 mg of the excipient of Example 2 is used.

EXAMPLE 9

Sustained-release tablets containing 40 mg metoclopramide were prepared with the following ingredients:

| Ingredient | % w/w |
| --- | --- |
| Metoclopramide Hydrochloride | 12.3 |
| Xanthan gum (Keltrol F) | 28.0 |
| Excipient of Example 1 | 43.9 |
| Polyvinylpyrrolidone (Plasdone K29-32) | 2.5 |
| Lactose BP | 12.3 |
| Stearic Acid | 1.0 |
| Isopropyl alcohol | q.s. |

The tablets are prepared as follows. The resultant tablets provide sustained-release of metocloramide. The metocloramide, 50% of the xanthan gum and the excipient of Example 1 are deaggregated through a 6 mesh screen into a blender and the powders are mixed for approximately 3 minutes at high speed. A solution of polyvinyl pyrrolidone in isopropyl alcohol was prepared and added to the mixing powders over a 30 second period. Further mixing and addition of isopropyl alcohol was carried out to produce suitable granules.

The wet granules mass was discharged through a 4 mesh screen into the drying bowl of a fluid bed dryer. The granules were dried until the moisture level reached below 1% w/w. The dry granules were sieved through a 16 mesh screen, weighed and blended with the remaining portion of the xanthan gum and stearic acid for 30 minutes and compressed on a tablet press to produce sustained release tablets containing 40 mg metoclopromide.

EXAMPLE 10

Sustained-release tablets containing 150 mg indomethacin were prepared in the same way as described in Example 9 from the following ingredients:

| Ingredient | % w/w |
| --- | --- |
| Indomethacin | 46.1 |
| Xanthan gum (Keltrol F) | 23.0 |
| Excipient of Example 1 | 15.0 |
| Polyvinylpyrrolidone (Plasdone K29-32) | 2.5 |
| Lactose | 12.3 |
| Isopropyl alcohol | q.s. |

EXAMPLE 11

Sustained-release tablets containing 300 mg theophylline were prepared in the same manner as described in Example 9 from the following ingredients:

| Ingredient | % w/w |
| --- | --- |
| Theophylline BP (anhydrous) | 46.1 |
| Xanthan gum | 28.0 |
| Excipient of Example 1 | 10.0 |
| Lactose BP | 12.3 |
| Polyvinylpyrrolidone | 2.5 |
| Stearic Acid | 1.0 |
| Isopropyl Alcohol | qs |

The resultant tablets provide sustained release of theophylline.

EXAMPLES 12–16

In examples 12–16, tablets are prepared similar to those in Example 9 except that an equal amount of the excipient of Example 2 is substituted for the excipient of Example 1. The resultant tablets provide sustained-release of the active ingredient.

EXAMPLES 17–21

In examples 19–23, tablets similar to those in Example 9 is prepared except that an equal amount of an excipient comprising microcrystalline cellulose, 0.25% w/w SLS and 5.0% colloidal silicon dioxide is substituted for Excipient 1. The resultant tablets provide sustained release of the active ingredient.

The preceding examples are not meant to be exclusive. Many other examples will be readily apparent to those skilled in the art and are contemplated to be encompassed by the scope of the claims appended hereto offered solely by way of explanation and are not intended to limit the scope of the appended.

We claim:

1. A method of preparing a sustained-released pharmaceutical formulation, comprising:

forming an aqueous slurry containing a mixture of microcrystalline cellulose and a compressibility augmenting agent which (i) physically restricts the proximity of the interface between adjacent cellulose surfaces, (ii) inhibits interactions between adjacent cellulose surfaces, or (iii) accomplishes both (i) and (ii) above;

drying said slurry to obtain an augmented microcrystalline cellulose comprising a plurality of agglomerated particles of said microcrystalline cellulose in intimate association with said augmenting agent;

adding an effective amount of an active agent to said slurry or said dried augmented microcrystalline cellulose; and incorporating an effective amount of a sustained-release carrier to obtain a final product which provides sustained-release of said active agent in an environment of use.

2. The method of claim 1, further comprising wet granulating said augmented microcrystalline cellulose and at least a portion of said sustained-release carrier to form a matrix.

3. The method of claim 1, further comprising incorporating said active agent into said matrix.

4. The method of claim 3, further comprising compressing said matrix to form a tablet.

5. The method of claim 3, further comprising coating said tablet with a portion of said sustained-release carrier.

6. The method of claim 1, further comprising compressing said excipient together with said therapeutic agent to form an immediate release core.

7. The method of claim 3, wherein said immediate release core is coated with at least a portion of said sustained-release carrier.

8. The method according to claim 1, wherein said compressibility augmenting agent is a surfactant included in an amount from about 0.1% to about 0.5% by weight, based on the weight of microcrystalline cellulose.

9. The method according to claim 1, further comprising the step of wet granulating said augmented microcrystalline cellulose with said sustained-release carrier.

10. The method according to claim 1, further comprising the step of wet granulating said augmented microcrystalline cellulose with said active agent.

11. The method according to claim 9, further comprising the step of compressing said active agent, augmented microcrystalline cellulose and said sustained-release carrier into a tablet.

12. The method according to claim 10, further comprising the step of compressing said active agent, augmented microcrystalline cellulose and said sustained-release carrier into a tablet.

13. The method according to claim 11, wherein said sustained-release carrier comprises a retardant selected from the group consisting of alkylcelluloses, acrylic and methacrylic acid polymers and copolymers, polylactides, polyglycolides, cellulose ethers, cellulose esters, polyanhydrides, polyorthoesters, polycaprolactones, polyphosphazenes, polysaccharides, proteinaceous polymers, polypeptides, polyesters, polyorthoesters, hydrophilic polymers, hydrophilic gums, waxes and wax-like materials, and mixtures thereof.

14. The method according to claim 12, wherein said sustained-release carrier comprises a retardant selected from the group consisting of alkylcelluloses, acrylic and methacrylic acid polymers and copolymers, polylactides, polyglycolides, cellulose ethers, cellulose esters, polyanhydrides, polyorthoesters, polycaprolactones, polyphosphazenes, polysaccharides, proteinaceous polymers, polypeptides, polyesters, polyorthoesters, hydrophilic polymers, hydrophilic gums, waxes and wax-like materials, and mixtures thereof.

15. The method according to claim 1, wherein said augmented microcrystalline cellulose includes a compressibility augmenting agent which inhibits interaction between adjacent cellulose surfaces via the creation the hydrophobic boundary at cellulose surfaces.

16. The method according to claim 10, further comprising the steps of compressing said augmented microcrystalline cellulose and said active agent into a tablet and applying said sustained-release carrier as a coating on said tablet.

17. The method of claim 1, wherein said compressibility augmenting agent is a surfactant having an HLB of at least about 10.

18. The method of claim 1, wherein said compressibility augmenting agent is a surfactant having an HLB of from about 15 to about 40.

19. The method of claim 1, wherein said compressibility augmenting agent is a silicon dioxide derived from a silicon dioxide having an average primary particle size from about 1 nm to about 100 nm.

20. The method of claim 1, wherein said silicon dioxide is included in an amount from about 0.1% to about 20% by weight, based on the weight of microcrystalline cellulose.

21. The method of claim 19, wherein said silicon dioxide is colloidal silicon dioxide.

22. The method of claim 1, wherein said compressibility augmenting agent is a surfactant.

23. The method of claim 22, wherein said compressibility augmenting agent is sodium lauryl sulfate.

24. The method of claim 1, wherein said compressibility augmenting agent is a polysorbate.

25. The method of claim 11, wherein said surfactant is included in an amount from about 0.1% to about 20% by weight, based on the weight of microcrystalline cellulose.

26. The method of claim 1, wherein said compressibility augmenting agent is a pharmaceutically acceptable highly polar compound.

27. The method of claim 26, wherein said highly polar compound is a suitable dye selected from the group consisting of 3,3'-[[1,1'Biphenyl]-4,4'-diylbis-(azo)]bis[4-amino-1-naphthalenesulfonic acid] disodium salt; disodium salt of 6-hydroxy-5[2(2-methyl-4-sulfophenyl)azo]-2-naphtalenesulfonic acid); 5-oxo-1-(p-sulfophenyl)-4-[(p-sulfophenyl)azo]-2-pyrazoline-3-carboxylic acid, trisodium salt); disodium salt of 1-p-sulphophenylazo-2-naphthol-6-sulfonic acid); trisodium-2-hydroxy-1-(4-sulfonato-1-naphthylazo)naphthalene-6,8-disulfonate); disodium 4,4'-(2,4-dihydroxy-5-hydroxymethyl-3,3-phenylene bisazo)di(napthalene-1-sulfonate)); tetrasodium 4-acetamido-5-hydroxy-6-[7-sulfonato-4-(4-sulfonatophenylazo)-1-Naphthylazo]naphthalene-1,7-disulfonate); disodium 4-hydroxy-3-(4-sulfonato-1-naphythylazo)naphthalene-1-sulfonate); trisodium 2-hydroxy-1-(4-sulfonato-1-naphthylazo)naphthalene-3,6-disulfonate); and mixtures thereof.

28. The method of claim 1, wherein said sustained-release carrier comprises a retardant selected from the group consisting of alkylcelluloses, acrylic and methacrylic acid polymers and copolymers, polylactides, polyglycolides, cellulose ethers, cellulose esters, polyanhydrides, polyorthoesters, polycaprolactones, polyphosphazenes, polysaccharides, proteinaceous polymers, polypeptides, polyesters, polyorthoesters, hydrophilic polymers, hydrophilic gums, waxes and wax-like materials, and mixtures thereof.

29. The method of claim 28, wherein said retardant is a hydrophilic gum.

30. The method of claim 28, wherein said retardant is a hydrophilic polymer.

31. The method of claim 1, which further comprises the steps of: forming an immediate release core comprising the augmented microcrystalline cellulose including the compressibility augmenting agent, and the effective amount of a therapeutic agent; and coating the core with at least a portion of the sustained released carrier.

32. The method of claim 31, wherein said step of forming said immediate release core includes forming said immediate release core as a tablet.

33. The method of claim 1, further comprising the step of forming a matrix including said augmented microcrystalline cellulose, at least a portion of said sustained release carrier, and said active agent.

34. The method of claim 33, further comprising the step of compressing said matrix into a tablet.

35. The method of claim 34, further comprising the step of coating the surface of the tablet with a portion of said sustained-release carrier.

36. The method of claim 33, wherein said compressibility augmenting agent is a highly polar compound, said highly polar compound being a suitable dye selected from the group consisting of 3,3'-[[1,1'Biphenyl]-4,4'diylbis-(azo)] bis[4-amino-1-naphthalenesulfonic acid] disodium salt; disodium salt of 6-hydroxy-5[2-methyl-4-sulfophenyl)azo]-2-naphthalenesulfonic acid); 5-oxo-1-(p-sulfophenyl)-4-[)p-sulfophenyl)azo]-2-pyrazoline-3-carboxylic acid, trisodium salt); disodium salt of 1-p-sulphophenylazo-2-naphthol-6-sulfonic acid); trisodium-2-hydroxy-1-(4-sulfonato-1-naphthylazo)naphthalene-6,8-disulfonate); disodium 4,4'-(2, 4-dihydroxy-5-hydroxymethyl-3,3-phenylene bisazo)di (napthalene-1-sulfonate)); tetrasodium 4-acetamido-5-hydroxy-6-[7-sulfonato-4-(4-sulfonatophenylazo)-1-naphthylazo]naphthalene-1,7-disulfonate); disodium 4-hydroxy-3-(4-sulfonato-1-naphythylazo)Naphthalene-1-sulfonate); trisodium 2-hydroxy-1-(4-sulfonato-1-naphthylazo)naphthalene-3,6-disulfonate); and mixtures thereof.

* * * * *